United States Patent [19]
Ginsburg

[11] Patent Number: 5,879,329
[45] Date of Patent: Mar. 9, 1999

[54] INFUSION SYSTEMS AND METHODS FOR INTRODUCING FLUIDS INTO THE BODY WITHIN A DESIRED TEMPERATURE RANGE

[75] Inventor: Robert Ginsburg, Greenwood Village, Colo.

[73] Assignee: Radiant Medical, Inc., Portola Valley, Calif.

[21] Appl. No.: 787,425

[22] Filed: Jan. 22, 1997

[51] Int. Cl.⁶ ...................................................... A61F 7/12
[52] U.S. Cl. .............................. 604/93; 604/408; 604/118
[58] Field of Search ................................... 604/113, 114, 604/118, 408; 607/96, 104, 105, 106

[56] References Cited

U.S. PATENT DOCUMENTS

| | | | |
|---|---|---|---|
| 3,902,635 | 9/1975 | Jinotti | 222/103 |
| 4,678,460 | 7/1987 | Rosner . | |
| 4,772,263 | 9/1988 | Dorman et al. . | |
| 4,981,135 | 1/1991 | Hardy | 128/402 |
| 5,061,241 | 10/1991 | Stephens, Jr. et al. | 604/114 |
| 5,101,804 | 4/1992 | Cohn . | |
| 5,125,900 | 6/1992 | Teves | 604/114 |
| 5,368,591 | 11/1994 | Lennox et al. . | |
| 5,437,673 | 8/1995 | Baust et al. . | |
| 5,567,136 | 10/1996 | Johnson . | |

*Primary Examiner*—Michael Buiz
*Assistant Examiner*—David O. Reip
*Attorney, Agent, or Firm*—Wilson Sonsini Goodrich & Rosati

[57] ABSTRACT

The invention provides systems and methods for infusing a fluid into a patient. In one exemplary embodiment, a system comprises a volume of fluid and a temperature altering device in close proximity to the volume of fluid. The temperature altering device is employed to heat or cool the volume of fluid to a desired temperature. A positive pressure device is provided to place the volume of fluid under positive pressure while at the desired temperature. A transfer member is further provided to transfer at least some of the fluid into the patient while at the desired temperature.

17 Claims, 2 Drawing Sheets

INFUSION SYSTEMS AND METHODS FOR INTRODUCING FLUIDS INTO THE BODY WITHIN A DESIRED TEMPERATURE RANGE

BACKGROUND OF THE INVENTION

The present invention relates generally to the introduction of various fluids into a patient, and more particularly to the alteration of the temperature of the fluids prior to their introduction so that the fluids are within a desired temperature range when introduced. In one particular aspect, the fluids are pressurized to facilitate their introduction into the patient at a desired rate and volume, thereby allowing the fluids to be introduced without relying on the assistance of gravity.

Various medical procedures rely on the introduction of different fluids into the body, often directly into the blood stream. In many cases, it is desirable to have such fluids introduced while the temperature of the fluids are within a desired range. For example, as described in copending U.S. application Ser. No. 08/769,931, filed Dec. 19, 1996, the complete disclosure of which is herein incorporated by reference, heated or cooled fluids may be introduced into a patient suffering from hypothermia or hyperthermia, or for neuro protection. Copending U.S. application Ser. No. 08/769,931, filed Dec. 19, 1996, describes various catheter embodiments which heat or cool a fluid while the fluid is within the patient. In this manner, a fluid may be heated to a desired temperature to raise the patient's core body temperature and thereby reduce or eliminate the symptoms of hypothermia. Alternatively, such catheter embodiments may be employed to cool the fluid while within the patient to lower the patient's core body temperature. Cooling of the fluid while within the patient may also be employed by such catheter embodiments to cool a specific region of tissue prior to performing a surgical procedure.

In many cases the treatment of a patient requires urgent medical attention and may therefore limit the types of equipment that may be used for treatment. For instance, in cases where the introduction of fluids into the patient is a prescribed treatment, the fluids must be introduced into the patient as quickly as possible. In such cases, it would therefore be desirable to provide a portable system that could be used in the field or in an ambulance to rapidly infuse various fluids which are within a desired temperature range into the patient.

Many existing fluid introduction systems rely on a gravity feed system where the fluid is held within a compressible structure, such as an IV bag. However, such gravity feed systems are often inconvenient in cases where urgent treatment is required, such as in the field or in tight spaces where elevation of the IV bag is impossible, e.g. in an ambulance. For example, without proper elevation, it is difficult to regulate the rate and volume of fluid introduction.

Another drawback of such gravity feed systems is the difficulty in regulating the temperature of the fluid within the IV bag. Hence, with such systems it is difficult to ensure the fluid is at the proper temperature when introduced into the patient.

Hence, for these and other reasons, it would be desirable to provide systems and methods which would place a fluid within a desired temperature range prior to its introduction into a patient. Such systems and methods should also be conducive to urgent care settings which require mobility, manipulation in tight spaces and rapid preparation. Such systems and methods should also be able to precisely control the rate and volume of fluid introduction into the patient. Further, in some cases it would be desirable if the systems and methods were able to place the fluids within the desired temperature range while the fluids are within conventional containers, such as IV bags.

SUMMARY OF THE INVENTION

The invention provides systems and methods for infusing fluids into a patient. According to the invention, the fluids may be infused into the patient in a variety of ways, including intraveneously, intra-arterially, peritoneally (intra-abdominally), and the like. In one exemplary embodiment, a system is provided comprising a volume of fluid, and a temperature altering device in close proximity to the volume of the fluid to heat or cool the fluid to a desired temperature. A positive pressure device is further provided to place the volume of fluid under positive pressure while at the desired temperature. A transfer member is provided to transfer at least some of the fluid into the patient while the fluid is at the desired temperature.

In one aspect of the system, the temperature altering device comprises a heater to heat the fluid to a temperature which is within the range from about 36° C. to about 42° C. Alternatively, the temperature altering device may comprise a cooler to cool the fluid to a temperature within the range from about 0° C. to about 35° C.

In another aspect, the system further includes a reservoir, such as a compressible bag, for holding the volume of fluid. The transfer member is operably connected to the reservoir, and a flow regulator is provided to regulate the flow of fluid from the reservoir and into the transfer member. The flow regulator preferably comprises a controller which regulate the application of pressure from the positive pressure device. In one particular aspect, the flow regulator will preferably regulate both the rate and volume of the fluid removed from the reservoir.

In still another aspect, the transfer member comprises a length of tubing to which an end dwelling device, such as a needle, catheter, sheath, or the like may be attached to infuse the fluid into the patient. In still another aspect, a controller is provided to monitor the temperature of the volume of fluid and to control actuation of the temperature altering device.

In one particular aspect, the temperature altering device comprises a housing having inner walls which define a chamber. The fluid is held within the chamber, and the housing includes temperature altering elements to heat or cool the inner walls of the housing to alter the temperature of the fluid. A variety of temperature altering elements may be provided to either heat or cool the inner walls such as electrical resistors, chemicals, frozen liquids, heated liquids, heated gases, radio frequency electrodes, thermoelectric crystals, and the like.

In another particular aspect, the positive pressure device comprises a plate and a compressor for moving the plate against the volume of fluid to compress the fluid. Exemplary compressors for moving the plate include springs, hydraulics, solenoids, and the like. Alternatively, the positive pressure device may comprise a bladder and a pressure source to expand the bladder against the volume of fluid.

The system may be employed to introduce a wide variety of fluids into the patient. Such fluids may include, for example, blood, saline solutions, drugs, solutes and the like.

The invention further provides an exemplary method for infusing a fluid into a patient. According to the method, a volume of fluid is provided and is at an initial temperature. The temperature of the fluid is altered until the fluid is at a desired temperature. While at the desired temperature, the fluid is pressurized to introduce the fluid into the patient at the desired temperature.

The pressure applied to the fluid will preferably be regulated so that the fluid is introduced into the patient at a predetermined rate and volume. In one exemplary aspect, the pressurized liquid is flowed through a tube which is intravenously inserted into the patient to introduce the fluid directly into the patient's blood stream.

In a further aspect, the fluid is heated to the desired temperature which is within the range from about 36° C. to about 42° C. Alternatively, the fluid may be cooled to the desired temperature which is in the range from about 0° C. to about 35° C. In one particularly preferable aspect, the temperature is altered by placing the volume of fluid into a housing having inner walls which define a chamber. The inner walls are then heated or cooled to alter the temperature of the fluid within the chamber.

In another particularly preferable aspect, the fluid is pressurized by compressing the volume of liquid with a plate. Alternatively, the fluid may be pressurized by inflating a bladder which presses against the volume of fluid. The volume of fluid may be selected from a wide variety of fluids including blood, saline solutions, drugs, solutes and the like. In one aspect, the volume of fluid will preferably be held within a compressible bag, with the temperature of the fluid being altered while within the bag.

DETAILED DESCRIPTION OF THE SPECIFIC EMBODIMENTS

The invention provides systems and methods for infusing various fluids which are at a desired temperature into a patient. In this way, the systems and methods may be used to treat a variety of ailments which require the infusion of a fluid while at a particular temperature. For example, the invention may be employed to heat a fluid to a temperature in the range from about 36° C. to about 42° C. and then inject the fluid directly into the blood stream to treat a patient suffering from hypothermia. Alternatively, the invention may be employed to cool a fluid to a temperature in the range from about 0° C. to about 35° C. and then inject the fluid directly into the blood stream to treat a patient suffering from hyperthermia. In an alternative aspect, the fluid may be cooled to a temperature in the range from about 0° C. to about 35° C. and injected into a vessel within the brain prior to a surgical procedure on the brain. Other applications with which the invention may be used include hypovolemia, cardiac arrest, stroke, and the like.

The systems and methods will preferably rely on the application of positive pressure to infuse the fluids into the patient's body. The application of such pressure will preferably be controlled so that the fluid is introduced at a predetermined rate and volume. In this manner, the fluids may be introduced without relying on a gravity feed system, such as is commonly employed when elevating IV bags to intravenously infuse various solutes into a patient. Such systems and methods are therefore advantageous in that they may be used in urgent care settings such as in the field or in an ambulance, where elevation of the fluid may be impossible or impractical.

The systems and methods of the invention will preferably be compatible for use with fluids which are contained within conventional storage containers, such as compressible bags, e.g. IV bags. In this manner, the fluids do not need to be transferred to a separate holder or container to facilitate heating or cooling. Rather, the fluids may be directly heated or cooled within their respective containers, thereby minimizing the time required to place the fluids at the desired temperature. The systems and methods of the invention may be employed to infuse a wide variety of fluids into a patient, including blood, saline solutions, drugs, solutes, and the like.

The system of the invention in some embodiments will preferably be portable so that it may be useful in field applications. In this manner, the systems may be transported to urgent care locations and used to treat the patient. Such portability may be provided by including a portable power supply, such as batteries, to supply power to the temperature altering device and to pressurize the fluid.

Figure 1:
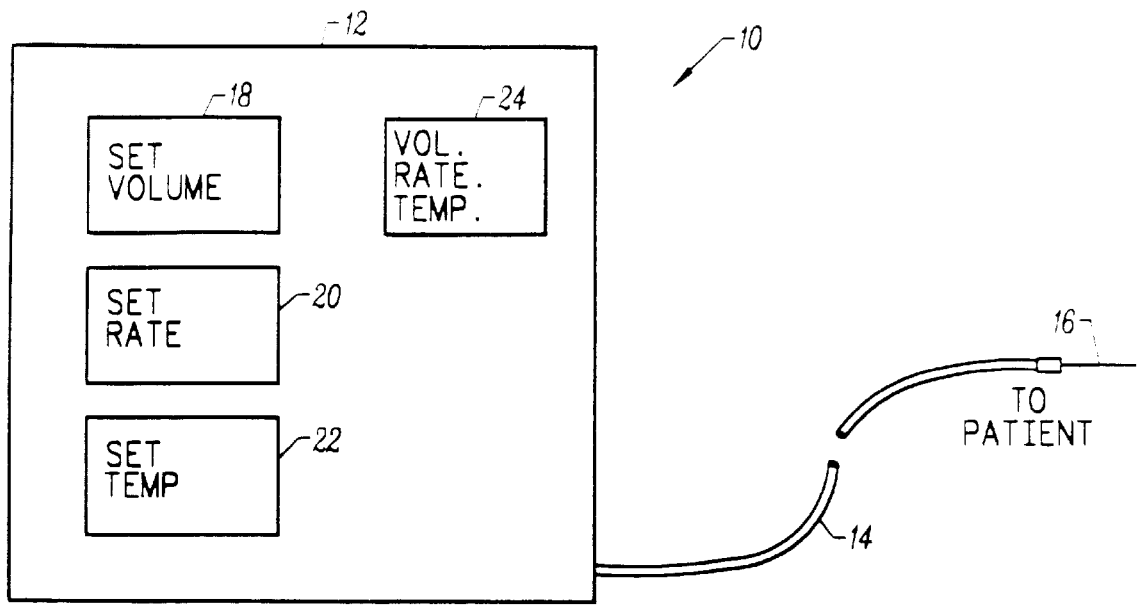
FIG. 1 is a schematic view of an exemplary system for infusing a fluid which is at a desired temperature into a patient according to the invention.

Referring now to FIG. 1, and exemplary system 10 for infusing a fluid into a patient will be described. System 10 includes a housing 12 into which a fluid is placed prior to introduction into the patient. The fluid exits housing 12 through a tube 14. A needle 16 is conveniently provided to intravenously introduce the fluid into the patient's blood stream. It will be appreciated, however, that a wide variety of end dwelling devices which are known in the art may be employed to place or infuse various fluids into a patient's body including, for example, sheaths, catheters, and the like. Such end dwelling devices may be employed to introduce the fluids into arteries, veins, other body lumens and sinuses, the abdominal cavity, and the like.

System 10 further includes a variety of switches, including a set volume switch 18, a set rate switch 20 and a set temperature switch 22. Switches 18, 20 and 22 may conveniently be configured as toggle switches to increase or decrease numerical values which are displayed on a screen 24. In this manner, a caregiver can quickly set the volume and rate of fluid flow as well as the temperature of the fluid using switches 18, 20 and 22. System 10 will further include a processor (not shown) which is in electrical communication with switches 18, 20 and 22 as well as screen 24. The processor will also be electrically connected to any pressure regulation devices used to control the volume and rate of fluid flow as well as any temperature altering elements used to alter the temperature of the fluid within housing 12 as described in greater detail hereinafter.

Figure 2:
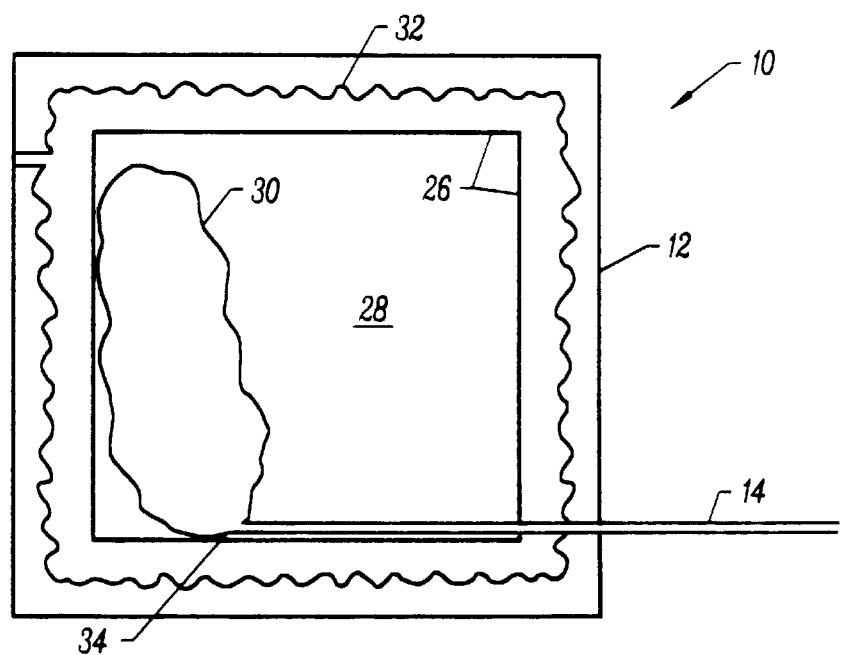
FIG. 2 is a cross-sectional side view of the system of FIG. 1 showing a temperature regulating element to regulate the temperature of a reservoir of fluid according to the invention.

Referring now to FIG. 2, a cross-sectional side view of system 10 will be described. As shown, housing 12 includes inner walls 26 which define a chamber 28 into which a reservoir 30 of fluid is placed. Reservoir 30 is connected to tubing 14 to allow the fluid to exit housing 12 through tubing 14. Reservoir 30 will preferably comprise a conventional container, such as a compressible bag, e.g., an IV bag, so that generally available fluids may rapidly be placed into housing 12 prior to their introduction into the patient.

Formed within housing 12 is a temperature altering element 32. As shown, temperature altering element 32 comprises an electrically resistive wire through which current may be passed to heat inner walls 26. In turn, heat from inner walls 26 is transferred to reservoir 30 to heat the fluid to a desired temperature. Power may be provided to temperature altering element 32 by a battery or by a separate AC or DC power source. Conveniently, a thermistor 34 is placed in contact with reservoir 30 to monitor the temperature of the fluid. Thermistor 34 will be in electrical communication with the processor so that actuation of temperature altering element 32 may be controlled to precisely control the temperature of the fluid within reservoir 30.

Although shown as an electrically resistive wire, various other temperature altering elements may be included within housing 12 to either heat or cool the fluid within reservoir 30. For example, other temperature altering elements may comprise various chemicals, frozen liquids, heated liquids, heated gases, radio frequency electrodes, thermoelectric crystals, and the like. One advantage of using various temperature altering elements is that certain elements may be used which do not require a stationary power source. In this manner, system 10 may be configured to be a portable system which may be used in the field without the need for connecting the system to a fixed electrical power source.

Figure 3:
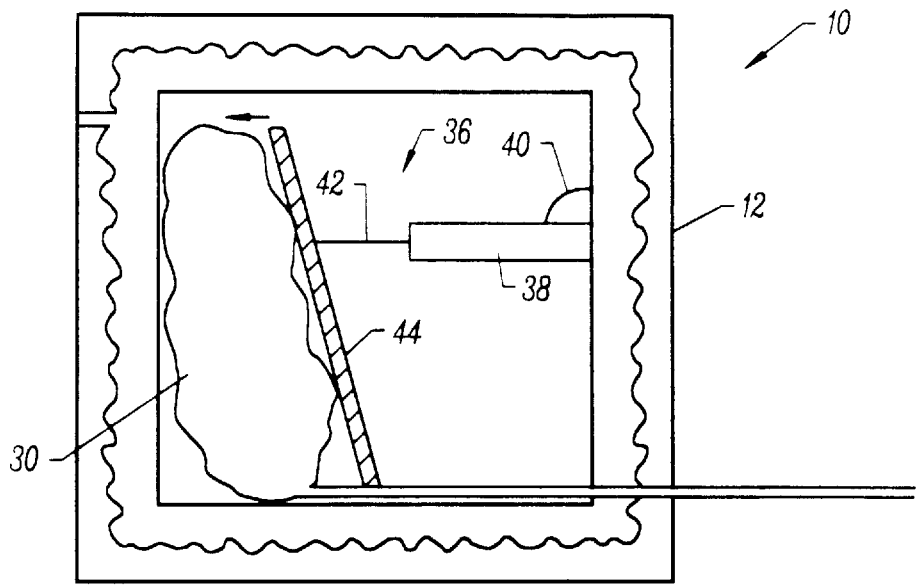
FIG. 3 illustrates the system of FIG. 2 with a compressor for pressurizing the reservoir of fluid according to the invention.

A variety of mechanisms may be employed to pressurize the fluid within reservoir 30 to control both the rate and volume of fluid which is infused into the patient. In this manner, fluids may be infused into the patient regardless of the elevation of housing 12. One exemplary embodiment of a compressor 36 that is used to pressurize the fluid within reservoir 30 is illustrated in FIG. 3. Compressor 36 comprises a solenoid 38 which is electrically connected to the processor by a wire 40 to control actuation of solenoid 38. Power may be supplied to solenoid 38 by a battery or separate power source as needed. Solenoid 38 includes a rod 42 which is translated to move a plate 44 against reservoir 30. The processor will preferably be employed to control the translation rate and displacement of rod 42 to control the rate at which the fluid is removed from reservoir 30 as well as the total volume removed from reservoir 30. In this way, once the fluid is at the desired temperature, solenoid 38 may be actuated at a given rate and for a given time to control the rate at which the fluid is introduced to the patient as well as the total volume of fluid that is introduced.

Figure 4:
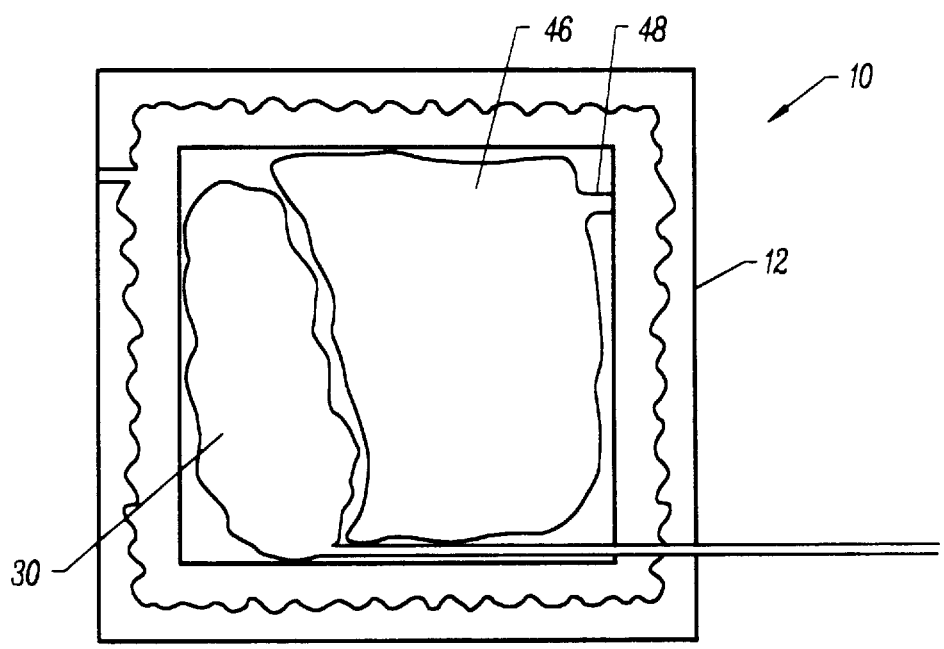
FIG. 4 illustrates the system of FIG. 2 with an alternative compressor for pressurizing the reservoir of fluid according to the invention.

Referring to FIG. 4, an alternative embodiment of a compressor 46 for pressurizing the fluid within reservoir 30 will be described. Compressor 46 comprises a bladder having an opening 48 into which a fluid may be introduced to expand the bladder. As the bladder is expanded, it comes into contact with reservoir 30 to pressurize the liquid within reservoir 30. A source of pressurized fluid (not shown) will preferably be connected to opening 48 and will be electrically connected to the processor to control the total rate and volume of fluid introduced into the bladder. In this way, the rate and the volume of fluid leaving reservoir 30 may be controlled.

Although FIGS. 3 and 4 show two embodiments of compressors it will be appreciated that other compressors for pressurizing the fluid within reservoir 30 may be provided, including hydraulics, pressurized gases, electromagnetic devices, and the like.

The invention has now been described in detail. However, it will be appreciated that certain changes and modifications may be made. Therefore, the scope and content of this invention are not limited by the foregoing description. Rather, the scope and content are to be defined by the following claims.

What is claimed is:

1. A controlled fluid infusion device comprising:
   a temperature controlled housing configured for containment of a compressible bag of fluid, wherein the housing includes a temperature altering device to alter the temperature of the fluid contained in said compressible bag to a preselected temperature, and a temperature sensor for monitoring the temperature of the fluid contained within said compressible bag;
   a pressurization device positioned within said housing to exert a positive pressure on said compressible bag; and
   a controller in communication with said housing for selectively activating said temperature device and said pressurization device to release a predetermined amount of fluid from said compressible bag of fluid when the temperature of the fluid reaches the preselected temperature.

2. A system as in claim 1, wherein the temperature altering device comprises a heater, and wherein the desired temperature is within the range from about 36° C. to about 42° C.

3. A system as in claim 1, wherein the temperature altering device comprises a cooler, and wherein the desired temperature is within the range from about 0° C. to about 35° C.

4. A fluid infusion system comprising:
   a thermal housing having a chamber configured for placement of a flexible fluid storage container formed with a transfer member for the release of fluid within said container, wherein said thermal housing includes a temperature altering device for heating or cooling the fluid contained within said container to a predetermined temperature;
   a positive pressure device positioned within said thermal housing that controllably expands to exert a pressurization force against said flexible fluid storage container housing to release fluid contained within said container; and
   a processor for controlling and monitoring the expansion of said positive pressure device within said thermal housing to provide a predetermined flow rate for the release of fluid from said flexible fluid storage container when the predetermined temperature is reached.

5. A system as in claim 4, further comprising a flow regulator to regulate the flow of the fluid from the container and into the transfer member.

6. A system as in claim 5, wherein the flow regulator comprises a controller which regulates the application of pressure from the positive pressure device.

7. A system as in claim 6, wherein the flow regulator regulates both the rate and the volume of fluid removed from the container.

8. A system as in claim 5, wherein the reservoir container is a compressible bag.

9. A system as in claim 4, wherein the transfer member comprises a length of tubing.

10. A system as in claim 4, wherein the processor is electrically connected to the positive pressure device to control the rate of fluid flow, and the temperature altering device to alter the temperature of the fluid within said container.

11. A portable infusion system for injecting a fluid into a patient comprising:
   an enclosed housing formed with a chamber to hold a fluid infusion bag;
   a temperature altering device positioned within said housing to change and to monitor the temperature of the fluid contained within said fluid infusion bag;

a pressure regulation device positioned within said housing to control and to monitor the pressure of the fluid contained within said fluid infusion bag; and a control system in communication with said temperature altering device and said pressure regulation device, wherein said control system directs said pressure regulation device to pressurize the fluid within said fluid infusion bag to infuse the fluid into a patient at a controlled rate with a preselected temperature.

12. A system as in claim 11, wherein the housing includes inner walls which define a chamber, wherein the fluid infusion bag is held within the chamber, and wherein the temperature altering device selectively heats or cools the inner walls of the housing to alter the temperature of the fluid within the fluid infusion bag.

13. A system as in claim 12, wherein the temperature altering device is selected from a group consisting of electrical resistors, chemicals, frozen liquids, heated liquids, heated gases, radio frequency electrodes, and thermoelectric crystals.

14. A system as in claim 11, wherein the pressure regulation device comprises a plate and a compressor for moving the plate against the fluid infusion bag to compress the fluid.

15. A system as in claim 14, wherein the compressor is selected from a group of compressors consisting of springs, hydraulics, and solenoids.

16. A system as in claim 11 wherein the pressure regulation device comprises a bladder and a pressure source to expand the bladder against the fluid infusion bag.

17. A system as in claim 11, wherein the fluid is selected from a group of fluids consisting of blood, saline solutions, drugs, and solutes.

* * * * *